United States Patent
Jordan et al.

(10) Patent No.: US 8,435,283 B2
(45) Date of Patent: May 7, 2013

(54) ANTI-MIGRATION FEATURES AND GEOMETRY FOR A SHAPE MEMORY POLYMER STENT

(75) Inventors: Gary Jordan, Litchfield, NH (US); Ron Sahatjian, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/139,042

(22) Filed: Jun. 13, 2008

(65) Prior Publication Data

US 2008/0319540 A1   Dec. 25, 2008

Related U.S. Application Data

(60) Provisional application No. 60/934,607, filed on Jun. 13, 2007.

(51) Int. Cl.
*A61F 2/82* (2006.01)

(52) U.S. Cl.
USPC .......................... 623/1.18; 623/1.15; 623/1.2

(58) Field of Classification Search .............. 623/1.11, 623/1.12, 1.13, 1.15, 1.49, 1.18, 1.2
See application file for complete search history.

(56) References Cited

U.S. PATENT DOCUMENTS

| | | | |
|---|---|---|---|
| 5,116,360 A * | 5/1992 | Pinchuk et al. ............ 623/11.11 |
| 5,290,295 A | 3/1994 | Querals et al. |
| 5,700,285 A | 12/1997 | Myers et al. |
| 5,725,547 A * | 3/1998 | Chuter ......................... 606/194 |
| 5,733,925 A | 3/1998 | Kunz et al. |
| 5,735,892 A | 4/1998 | Myers et al. |
| 5,954,744 A | 9/1999 | Phan et al. |
| 6,716,239 B2 | 4/2004 | Sowinski et al. |
| 6,800,089 B1 | 10/2004 | Wang |
| 6,974,472 B2 * | 12/2005 | Hong et al. .................. 623/1.15 |
| 7,799,068 B2 * | 9/2010 | Holman et al. .............. 623/1.25 |
| 2001/0010012 A1 * | 7/2001 | Edwin et al. ................. 623/1.13 |
| 2002/0198586 A1 * | 12/2002 | Inoue ........................... 623/1.13 |
| 2003/0004563 A1 * | 1/2003 | Jackson et al. ............... 623/1.15 |
| 2003/0017775 A1 | 1/2003 | Sowinski et al. |
| 2003/0208256 A1 * | 11/2003 | DiMatteo et al. ............. 623/1.11 |
| 2004/0034403 A1 * | 2/2004 | Schmitt ......................... 623/1.2 |
| 2004/0098090 A1 | 5/2004 | Williams et al. |
| 2004/0182511 A1 | 9/2004 | Rakos et al. |
| 2004/0193262 A1 | 9/2004 | Shadduck |
| 2004/0236400 A1 * | 11/2004 | Edwin et al. ................. 623/1.12 |
| 2005/0010275 A1 | 1/2005 | Sahatjian et al. |

(Continued)

FOREIGN PATENT DOCUMENTS

WO   WO 2007/115208 A2   10/2007

OTHER PUBLICATIONS

International Search Report for PCT/US2008/066935.

(Continued)

*Primary Examiner* — Thomas J Sweet
*Assistant Examiner* — Seema Mathew
(74) *Attorney, Agent, or Firm* — Vidas, Arrett & Steinkraus, P.A.

(57) ABSTRACT

A radially-expandable stent for implantation in a bodily passageway, being expandable from an initial unexpanded state to an expanded state, having an outer surface with a geometric pattern covering said outer surface to minimize migration after implantation is provided. Also provided is a method of manufacturing such a stent.

8 Claims, 4 Drawing Sheets

U.S. PATENT DOCUMENTS

| | | | |
|---|---|---|---|
| 2005/0256564 A1* | 11/2005 | Yang et al. | 623/1.42 |
| 2007/0023951 A1 | 2/2007 | Williams et al. | |
| 2007/0123969 A1* | 5/2007 | Gianotti | 623/1.2 |
| 2010/0030321 A1* | 2/2010 | Mach | 623/1.18 |
| 2010/0100170 A1* | 4/2010 | Tan et al. | 623/1.18 |
| 2012/0191171 A1* | 7/2012 | Milijasevic et al. | 623/1.11 |
| 2012/0330402 A1* | 12/2012 | Vad et al. | 623/1.13 |

OTHER PUBLICATIONS

International Preliminary Report on Patentability (including Written Opinion of the International Searching Authority) for PCT/US2008/066935.

* cited by examiner

ANTI-MIGRATION FEATURES AND GEOMETRY FOR A SHAPE MEMORY POLYMER STENT

CROSS-REFERENCE TO RELATED APPLICATION

This patent application claims priority to and the benefit of U.S. Provisional Patent Application No. 60/934,607 filed Jun. 13, 2007 which is hereby incorporated by reference herein.

FIELD OF THE INVENTION

This invention relates to a shape memory stent having features and geometry on the stent's outer surface specifically adapted to minimize migration of the stent once it has been implanted and a method of manufacturing thereof.

BACKGROUND OF THE INVENTION

Stents are often used in the gastrointestinal tract to treat malignant or benign strictures as palliative or supporting treatment to chemotherapy or surgery. With biliary stent applications, plastic stents are often used. Plastic stents are typically have an outer diameter of 3.5 mm and an inner diameter of 2.5 mm and need to be exchanged relatively often (e.g., every three months) due to occlusion from bile. However, an advantage of plastic stents, besides their lower cost, is that their relative small size enables their use within and endoscopy instrument or endoscope. Conversely, self expanding metal stents (SEMS), are also useable and tend to have a longer patency than plastic stents because of their larger diameters, typically 8-10 mm, and having a further advantage that metal stents are collapsible from a larger to smaller diameter and may fit within and endoscope, and then expanded to a larger diameter. However, plastic stents are removable, whereas, metal stents generally are not. Common practice calls for removing stents when treatment of benign strictures is completed.

Accordingly, metal stents are generally restricted to use where malignant, not benign, strictures are present. In addition to the problems of permanency of metal stents, their costs are 10 to 15 times higher than plastic stents.

Because of inherent material deficiencies, plastic stents cannot be made and reliably used, having larger diameters that collapse down to small diameters and retaining good compression resistance as with self expanding metal stents. A need had developed for a stent having inner and outer diameters in a range similar to metal stents, e.g., 8-10 mm, yet have a low entry profile, and also be removable. SMP stents satisfy this need with SMP stents both being useable at the relatively large diameters, thereby providing good patency, and being removable, thus allowing for use with both benign and malignant applications. Additionally, a major benefit of SMP stents is that they are collapsible to a small diameter for insertion into a lumen of a patient, but can then be expanded like a metal stent once inside a patients lumen and then have the functional characteristics of a plastic stent.

SMP stents are preferably formable as tubular structures (which may be etched) or as coiled structures resembling coil springs. With either configuration, a straight, generally cylindrical shape may not be desired, due to the possibility of migration within a bodily passageway. A method has been developed of pre-forming SMP stents with one or both ends flared, with the SMP stents recovering this configuration in vivo at the point of implantation. However, in preparing the SMP stents, the stents are initially pre-formed with the flared-end configuration and then contracted to a minimized diameter for insertion into a catheter (in being readied for implantation). The contracted profile of the SMP stents resembles proportionately the profile of the fully-expanded stents, with the ends being likewise flared. With the smallest possible profile being sought for insertion into a patient, the flared-end configurations of the contracted SMP stents may be undesirable. Another method of minimizing migration of an SNIP stent is to form the stent with the inclusion of a shaped or textured outer surface, which therefore provides mechanical connection between the stent and the luminal surface of the vessel where the stent is implanted.

SUMMARY OF THE INVENTION

The present invention may utilize a modification of the stent's outer surface with features such as coils, rings, mesh and other surfaces to provide a mechanical bonding surface. One embodiment of the present invention therefore relates to a radially-expandable implant for implantation in a bodily passageway, being at least partially expandable from an initial unexpanded state to an expanded state, having an outer surface with a geometric pattern covering said outer surface to minimize migration after implantation.

In another embodiment, the invention comprises a geometric cross section that interacts with a body lumen to limit migration of an implant. For example, in a round or square stent, the implant may have at least one surface feature such as a protrusion from the outer wall for mechanically interacting with the a body lumen. Alternately, the stent may be of an undulating shape with directional surface features which inhibit motion in one direction while allowing transportability/flexibility in the other direction.

The stent of the current embodiment is useable in various bodily passageways for implanting a stent, including the gastrointestinal tract (e.g., bile ducts, colon, duodenum), esophagus, trachea, urine tract (e.g., urethra, prostate) and vasculature (e.g., coronary blood vessels, peripheral blood vessels, intracranial blood vessels).

These and other features will be better understood through a study of the following detailed description and accompanying drawings.

DETAILED DESCRIPTION OF THE INVENTION

In accordance with one embodiment of the present invention, the implant comprising a stent can be manufactured by utilizing an injection molding process. By utilizing this process, a particular surface geometry of the stent can be controlled by cutting the inverse geometric configuration into the inner diameter of the mold. The inner surface of the mold can contain any of various geometrical patterns such as a helical coil, mesh, rings or rough textured surface, as shown in the accompanying figures. Any change in geometry on the exterior wall of the implant may minimize migration while preferably preventing tissue damage in situ or upon removal. Additionally one embodiment of the present invention allows fluids from either the pancreatic duct or cystic duct to pass between the wall of the bile duct and the outer surface of the stent, should the stent pass over these ducts.

In one embodiment, the invention comprises a stent and, more preferably, a stent suited for placement within the gastrointestinal tract of an animal or human. In a further embodiment, the GI tract comprises the pancreatic duct, cystic duct or common bile duct. In yet a further embodiment, the outer surface of the implant comprises at least one surface modification to assist in limiting the potential migration of the implant within the body lumen.

Figures 1A, 1B, 1C:
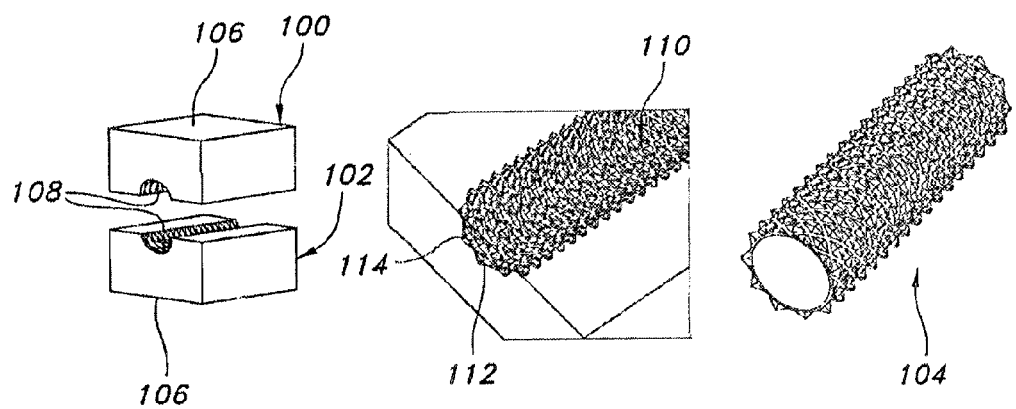
FIGS. 1A, B, and C are a schematic of an assembly including a mold and stent in accordance with the present invention having a particular externally extending outer geometry.

FIG. 1A illustrates a mold comprising a top portion 100 and a bottom portion 102. The top portion may comprise an inner and outer surface, wherein the inner surface may be adapted to receiving material for the manufacture of the stent according to the present invention. The stent 104 may be formed as a hollow structure, which may be etched, or may be formed as a coiled structure resembling a coil spring. U.S. patent application Ser. No. 10/683,314, filed Oct. 10, 2003 (published Jan. 13, 2005 as U.S. Publication No. 2005-0010275 A1), disclose suitable materials and geometries for Shape Memory Polymer (hereinafter SMP) stents. The entire disclosures of U.S. patent application Ser. No. 10/683,314 are incorporated by reference herein.

In one embodiment, the stent 104 comprises an SMP. Examples of SMP's include polynorbornene and copolymers of polynorbornene, blends of polybornene with KRATON® (thermoplastic elastomer) and polyethylene, styrenic block copolymer elastomers (e.g., styrene-butadiene), polymethylmethacrylate (PMMA), polyethylene, polyurethane, polyisoprene, polycaprolactone and copolymers of polycaprolactone, polylactic acid (PLA) and copolymers of polyactic acid, polyglycolic acid (PGA) and copolymers of polyglycolic acid, copolymers of PLA and PGA, polyenes, nylons, polycyclooctene (PCO), polyvinyl acetate (PVAc), polyvinylidene fluoride (PVDF), blends of polyvinyl acetate/polyvinylidine fluoride (PVAc/PVDF), blends of polymethylmethacrylate/polyvinyl acetate/polyvinylidine fluoride (PVAc/PVDF/PMMA) and polyvinylchloride (PVC) and blends and/or combinations thereof.

The implant 104, comprising SMP, may be pre-formed to an initial diameter and then may be heated, to a temperature that may be near or above the melt or glass transition. It may then be mechanically deformed to a smaller, contracted profile, suitable for delivery into the body of a patient. The implant 104 is cooled and for implantation may be assembled onto a catheter (not shown), or other delivery system and delivered into the body of a patient. The implant may then be expanded with application of heat to the melt or glass transition.

In some embodiments a balloon may be used to expand a portion of the implant 104 to a profile greater than the pre-formed reduced profile. As such, the implant 104 may be deformed in vivo at the point of implantation. The implant 104 may be pre-formed with a smaller overall profile for implantation. In some embodiments, the implant 104 may be pre-formed with a geometric pattern on the outside surface of the stent. The pattern may become more prominent when the implant 104 is expanded to a final configuration. In the reduced profile of the implant 104 may be minimized, yet some memory may be imparted to the s implant 104 to aid in formation of the geometric shape. In some embodiments, implant 104 is not reduced in profile.

Additionally, a stent may be removable, through the use of SMP. The implant 104 may be manufactured as a small diameter and put on the balloon, and then expanded to a large diameter when implanted in the body. Subsequently, the stent may be removed by reintroducing heat into the stent, which will cause the stent to shrink to its original smaller diameter, thus facilitating removal through a catheter, or endoscopy instrument. Some implants may not be totally formed of SMP. SMP may provide a support structure or scaffold with another expandable material combined, or laid over or within the implant.

An SMP stent and a graft may be combined into a stent-graft endoprosthesis to combine the features and advantages of each. For example, tubular coverings have been provided on the inner and/or outer surfaces of stents to form stent-grafts. It is often desirable to use a thin-walled graft or covering in the stent-graft endoprosthesis to minimize the profile of the endoprosthesis and to maximize the flow of blood through the endoprosthesis. In such cases non-textile materials, such as polymeric tubes or sheets formed into tubes, are often used.

Expanded polytetrafluoroethylene or e-PTFE is one common polymeric material used as the graft portion or covering of a stent-graft endoprosthesis. Expanded polytetrafluoroethylene grafts, however, are subject to plastic deformation, especially when, for example, compressing the stent-graft for loading into its delivery system, delivering the stent-graft through a highly tortuous bodily lumen and/or placing or deploying the stent-graft at the target implant site. Such plastic deformation may lead to the tearing of the ePTFE, leaving the stent-graft endoprosthesis prone to leakage of blood therethrough. Furthermore, plastic deformation of expanded polytetrafluoroethylene grafts may lead to physical deformities in the graft, such as buckling, which is also undesirable because it may lead to poor blood flow patterns.

Sheets or films of ePTFE have been used to cover or line stents. For example, U.S. Pat. Nos. 5,700,285 and 5,735,892 to Myers et al. describe overlapping a sheet of ePTFE onto a stent to form a tubular graft. The graft is secured to the stent by an application of thermoplastic adhesive and heat treatment to melt the adhesive. A seam, which is formed where the sheet overlaps, is also sealed through the use of the thermoplastic adhesive.

In one embodiment, the stent may be manufactured by utilizing an injection molding process. A desired surface geometry of the implant can be controlled by cutting the inverse geometry into the inner surface of a mold. SMP may be injected into the mold. An inner surface of this mold may contain any of various geometrical patterns including a helical coils, meshes, rings or a rough textured surface; which will be further illustrated in FIGS. 1-4. Such geometries, or other patterns may permit bodily tissue such as a body lumen to engage in recesses of the pattern. This type of engagement may help minimize migration of the stent and may reduce tissue damage. Furthermore, tissue damage may be reduced in repository or removal procedures.

An alternate method of manufacturing implant 104 with a surface modification may include extruding the tubing to a constrained diameter. A reduced profile plug of SMP may be placed inside a mold. The plug may then be expanded within a mold having a pattern. The mold may have exit points to permit flow of the SMP out of the mold as one manner to control the volume of SMP within the mold.

In another alternate method of manufacture, the implant 104 may be formed by molding the exterior surface modification onto a separate layer of material, such as for example a non-textile material. As used herein, the term "non-textile" and its variants refer to a material formed by casting, molding, spinning or extruding techniques to the exclusion of typical textile forming techniques, such as braiding, weaving, knitting and the like. Nonlimiting examples of useful polymeric materials for the non-textile polymeric graft portions include polyesters, polypropylenes, polyethylenes, polyurethanes, polynaphthalenes, polytetrafluoroethylenes, expanded polytetrafluoroethylene, silicone, and combinations and copolymers thereof. Desirably, the polymeric material polytetrafluoroethylene (PTFE), including expanded polytetrafluoroethylene (ePTFE).

PTFE exhibits superior biocompatibility and low thrombogenicity, which makes it particularly useful as vascular graft material in the repair or replacement of blood vessels or other bodily lumens. Desirably the non-textile layer is a tubular structure manufactured from ePTFE. The ePTFE material has a fibrous state which is defined by interspaced nodes interconnected by elongated fibrils. The space between the node surfaces that is spanned by the fibrils is defined as the internodal distance. When the term expanded is used to describe PTFE, it is intended to describe PTFE which has been stretched, in accordance with techniques which increase the internodal distance and concomitantly porosity. The stretching may be in uni-axially, bi-axially, or multi-axially. The nodes are spaced apart by the stretched fibrils in the direction of the expansion.

Desirably, the ePTFE material is a physically modified ePTFE tubular structure having enhanced axial elongation and radial expansion properties of up to about 2,000 percent by linear dimension, for example, from about 100 percent by linear dimension to about 2,000 percent by linear dimension, from about 100 percent by linear dimension to about 600 percent by linear dimension, from about 600 percent by linear dimension to about 2,000 percent by linear dimension, and the like. Such expansion properties are provided as exemplary characteristics and are do not limit the extent of elongation in any manner. Such physically modified ePTFE material may be made by reorienting the node and fibril structure through application a radially expansive and longitudinally foreshortening force. The physically modified ePTFE tubular structure is able to be elongated or expanded and then returned to its original state without an elastic force existing therewithin. Additional details of the physically modified ePTFE and methods for making the same can be found in U.S. Pat. No. 6,716,239, the contents of which are incorporated by reference herein.

The non-textile, polymeric implant layer may be secured to a SMP implant scaffold structure 104 through any suitable means, including, without limitation, lamination, such as heat and/or pressure lamination, and/or adhesive bonding. The bonding agent may include various biocompatible, elastomeric bonding agents such as urethanes, styrene/isobutylene/styrene block copolymers (SIBS), silicones, and combinations thereof. Other similar materials are contemplated. Desirably, the bonding agent may include polycarbonate urethanes sold under the trade name CORETHANE®. This urethane is provided as an adhesive solution with preferably 7.5% Corethane, 2.5 W30, in dimethylacetamide (DMAc) solvent. Details of suitable bonding agents and methods for bonding are further described in U.S. Patent Application Publication Nos. 2003/0017775 A1 and 2004/0182511 A1, the contents of which are incorporated herein by reference.

In another alternate method of manufacture, the implant 104 may be formed by attaching a first layer of non-textile material to the exterior of the SMP scaffold and second layer of non-textile material to the exterior surface of the first layer of non-textile material. The first and second layers may be of a non-textile polymeric material as described above and attached to a scaffold as described above. Additionally, however, in this alternate embodiment, the second layer may have externally extending features which are created on the exterior of the second layer after it is attached to the first layer. The externally extending features may be created by removing material from the second layer by any suitable method, for example by laser cutting, chemical etching, electrochemical etching, and the like.

FIG. 1 illustrates a mold top portion 100 and a bottom portion 102. The top portion 100 and bottom portion 102 may have an exterior 106 and interior 108 surface. The interior 108 surface of both the top 100 and bottom 102 portions may be adapted to receive a shape memory polymer material for a molding process., FIG. 1A illustrates the interior 108 surface of bottom portion 102 of a mold, wherein the mold comprises an inverse geometry textured surface or other surface modification. In one embodiment a textured surface comprises a diagonal cross hatch pattern 110, made up of overlapped rows 112 and 114 which are diagonally disposed to each other. A recess may be formed in the mold between two successive pairs of diagonally rows 112 and 114. As illustrated in FIG. 1 C, a mold may be an inverse of the implant. The mold may comprise recesses which inversely results in a raised regions of the implant 104. In one embodiment the surface modifications comprise a pyramid-like shape when the molding process is complete. Of course one skilled in the art will recognize the pattern described can be varied in various ways. For example, one variation may include changing the angle at which the diagonally disposed rows cross one another. Furthermore the depth of the raised region may be increased or decreased and the shape may be changed. For example, the raised region may have a pointed shape or alternately a curved convex shape. Furthermore, the rough textured surface could be made of an entirely different shape not incorporating the diagonal rows or raised pyramid-like shaped regions. For example, the raised regions may have a hemispherical or other curved shape.

Figures 2A, 2B, 2C:
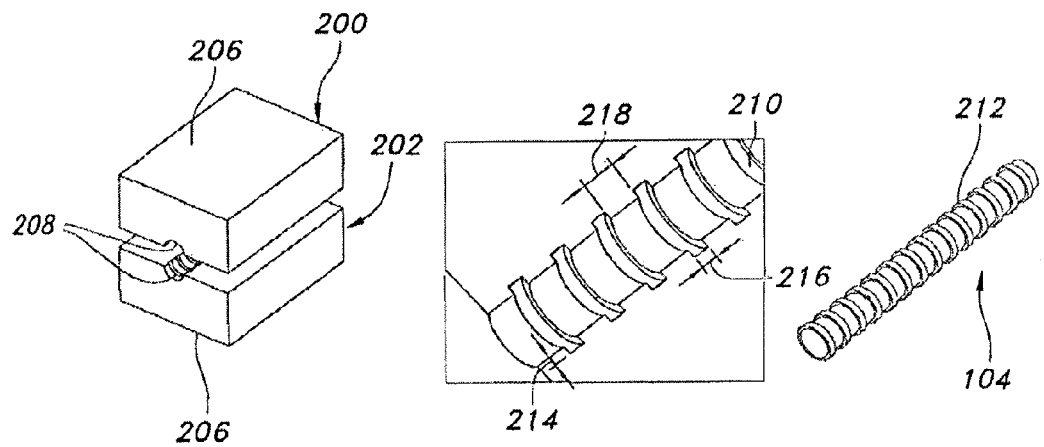
FIGS. 2A, B, and C are a schematic of an assembly including a mold and stent in accordance with the present invention having a particular externally extending outer geometry.

FIG. 2A illustrates a mold top portion 200 and a bottom portion 202. The top portion 200 and bottom portion 202 may have an exterior 206 and interior 208 surface. An interior 208 surface of both the top 200 and bottom 202 portions may be adapted to receive a shape memory polymer material. FIG. 2B illustrates the interior 208 surface of bottom portion 202 of the mold. In one embodiment, the mold may comprise the inverse geometry of a rings 210. In the particular embodiment depicted, the rings may comprise a pattern of annular rings 210 disposed about the circumference of the mold interior 208 perpendicular to the longitudinal axis of the mold. rings 210 may have a depth 214, longitudinal distance 216 and longitudinal separation distance 218.

FIG. 2C illustrates a mold being an inverse of an implant and further comprising annular rings. Annular rings may result results in a raised pattern 212. One skilled in the art will recognized the pattern described can be varied by changing the depth 214, longitudinal length 216 of the annular rings 210, or the spacing 218 between each ring angle. Variations may include varying the longitudinal distance of the annual rings to make them shorter or longer in accordance with the needs of the particular application. Likewise, the longitudinal distance between each ring may be varied, such that the rings may be separated by a longer or shorter distance. Furthermore, the ring shape could be varied such that the rings are not aligned with the longitudinal axis of the implant. For example, the rings may be arranged at an angle to the longitudinal axis of the implant wherein the annual rings are parallel. In another embodiment, the rings may be arranged at a varying angle to the longitudinal axis, such that the annular rings are not parallel to each other along the longitudinal axis of the implant.

Figures 3A, 3B, 3C:
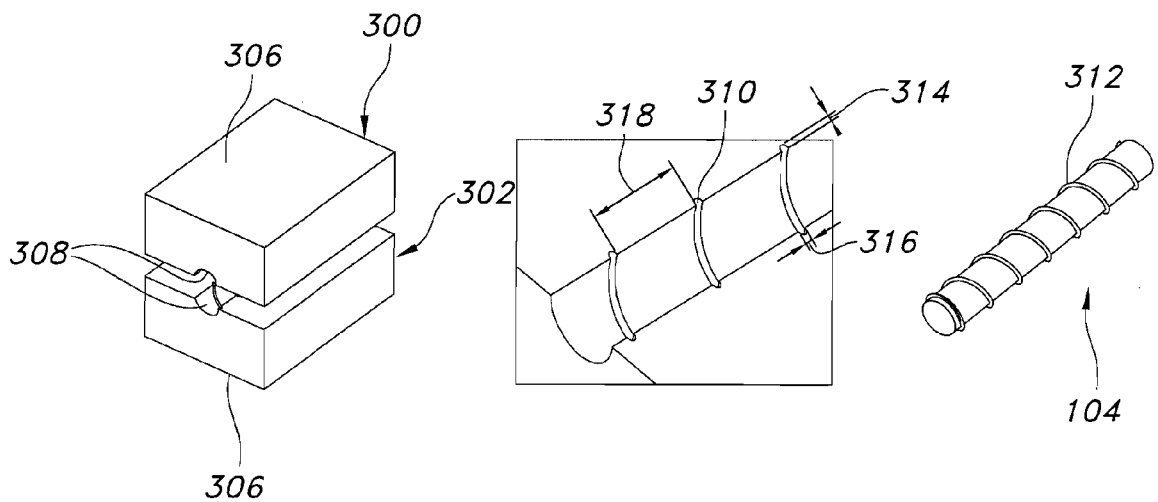
FIGS. 3A, B, and C are a schematic of an assembly including a mold and stent in accordance with the present invention having a particular externally extending outer geometry.

FIG. 3A comprises a mold top portion 300 and a bottom portion 302. The top portion 300 and the bottom portion 302 may have an exterior 306 and interior 308 surface. The interior 308 surface of both the top 300 and bottom 302 portions may be adapted to receive a shape memory polymer material. FIG. 3B illustrates the interior 308 surface of bottom portion 302 of a mold The mold may comprise the inverse geometry of helical rings 310. The rings may comprise a pattern of helical rings 310 disposed about the mold interior 308 diagonally to the longitudinal axis of the mold. Rings 310 may comprise a depth 314, longitudinal distance 316 and longitudinal separation distance 318. FIG. 3C illustrates, the mold being an inverse of an implant, Helical rings may results in a raised annular pattern 312. Of course, one skilled in the art will recognized the pattern described can be varied by changing the depth 314, longitudinal length 316 of the helical rings 310, or the spacing 318 between each ring angle. Furthermore, the angle of the helix can be varied to result in greater or lesser helical pitch. For example, the inverse helical pattern may be varied by altering the pitch angle of the spiral around the longitudinal axis of the implant. The angle may vary infinitely from a very shallow slope, nearly orthogonal to the longitudinal axis, to a very steep slope, i.e. nearly parallel to the longitudinal axis. In addition, the spacing between the helical rings may be varied such that the number of helical spirals per unit of longitudinal distance may be increased or decreased. Other variations may include altering the ring depth such that the raised helical pattern extends from the implant wall to a varying degree.

Figures 4A, 4B, 4C:
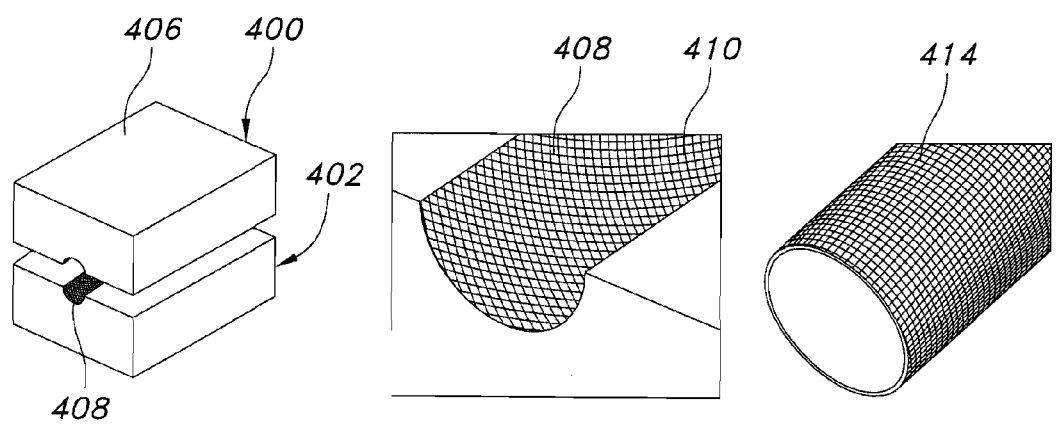
FIGS. 4A, B, and C are a schematic of an assembly including a mold and stent in accordance with the present invention having a particular externally extending outer geometry.

FIG. 4A illustrates a mold top portion 400 and a bottom portion 402. Top portion 400 and bottom portion 402 may have an exterior 406 and interior 408 surface. Interior 408 surface of both the top 400 and bottom 402 portions may be adapted to receive a shape memory polymer material. FIG. 4B illustrates an interior 408 surface of bottom portion 402 of a mold. Mold may have an inverse geometry of a mesh pattern. Mesh pattern surface may comprise a cross hatch of overlapped columns and row 410, which may be disposed along the length of the mold interior surface 408. As depicted in FIG. 4C, the mold is an inverse of the stent, the cross hatch of overlapped columns and row 410 results in a raised mesh pattern 414 when the molding process is complete on the exterior of the stent. Of course one skilled in the art will recognized the pattern described can be varied by changing the angle or spacing between the rows and column that form the mesh pattern.

For any of the raised patterns molded into the implant described above, alternate embodiment may be configured wherein the externally extending raised patterns, such as for example, a textured surface, annular rings, helical rings and a mesh pattern may be limited to only a portion of the exterior surface of the implant. For example, the implant may have the externally extending raised patterns limited longitudinally, circumferentially or in both directions.

Figure 5:
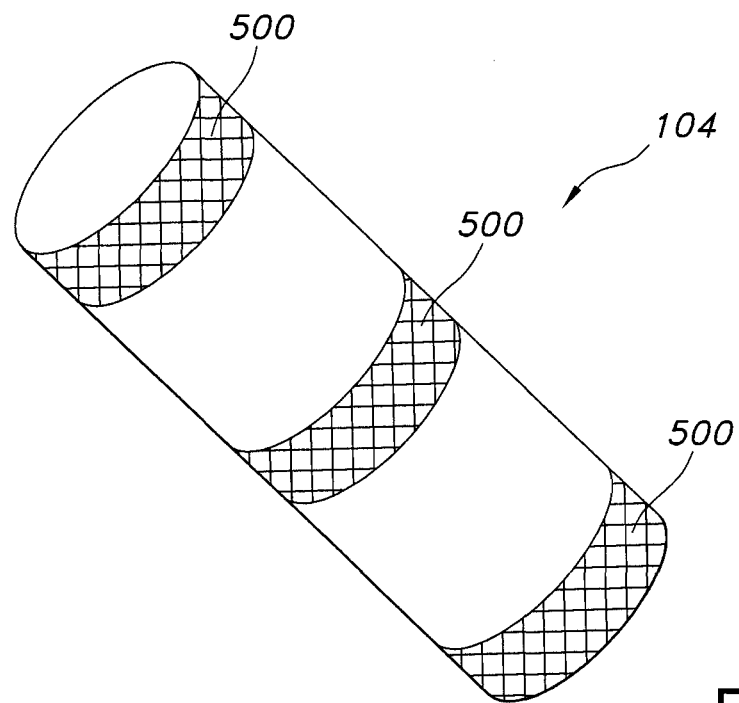
FIG. 5 depicts an alternate embodiment of the implant according to the present invention having circumferential sections of an externally extending outer geometry.

More specifically, FIG. 5 illustrates the implant 104 wherein the raised features 500 may be placed around the entire circumference of the implant, and within discrete longitudinal segments, such as only at the ends of the implant or in a repeating interval pattern.

Figure 6:
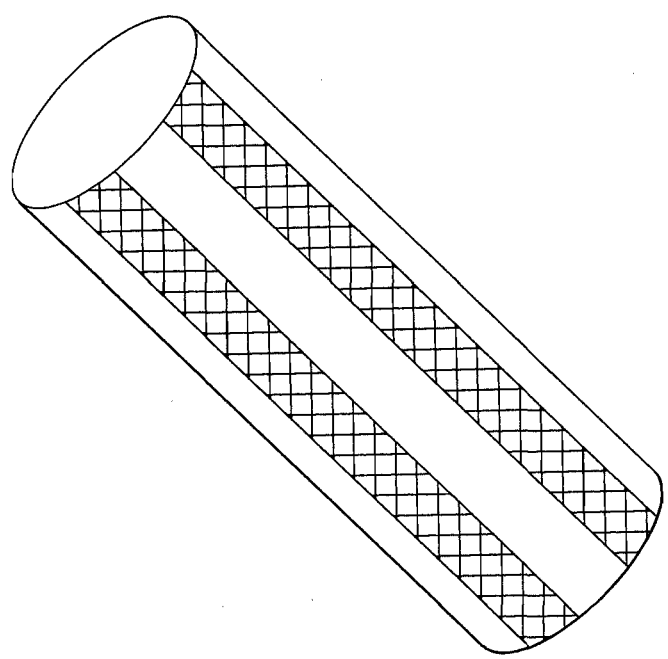
FIG. 6 depicts an alternate embodiment of the implant according to the present invention having longitudinal sections of an externally extending outer geometry.

FIG. 6 illustrates another alternative, which may include placing the raised features along the entire longitudinal length of the implant and within discrete circumferential portions, such as having one or more longitudinal discrete strips 502 of a raised feature from end to end and placed at intervals around the circumference of the implant.

Figure 7:
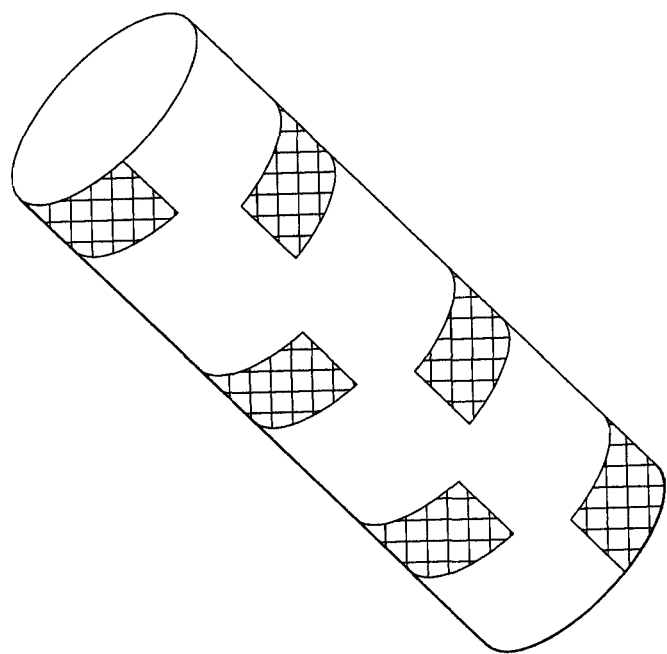
FIG. 7 depicts an alternate embodiment of the implant according to the present invention having discrete discontinuous sections of an externally extending outer geometry.

FIG. 7 illustrates another alternative, which may include placing the raised features along both discrete portions of the longitudinal length of the implant and within the discrete circumferential portions, such as having one or more longitudinal discrete sections of a raised feature positioned in discontinuous sections along the implant and around the circumference of the implant.

Stent 104 may be treated with a therapeutic agent or agents. "Therapeutic agents", "pharmaceuticals," "pharmaceutically active agents", "drugs" and other related terms may be used interchangeably herein and include genetic therapeutic agents, non-genetic therapeutic agents and cells. Therapeutic agents may be used singly or in combination. A wide variety of therapeutic agents can be employed in conjunction with the present invention including those used for the treatment of a wide variety of diseases and conditions (i.e., the prevention of a disease or condition, the reduction or elimination of symptoms associated with a disease or condition, or the substantial or complete elimination of a disease or condition).

Non-limiting examples of useful therapeutic agents include, but are not limited to, adrenergic agents, adrenocortical steroids, adrenocortical suppressants, alcohol deterrents, aldosterone antagonists, amino acids and proteins, ammonia detoxicants, anabolic agents, analeptic agents, analgesic agents, androgenic agents, anesthetic agents, anorectic compounds, anorexic agents, antagonists, anterior pituitary activators and suppressants, anthelmintic agents, anti-adrenergic agents, anti-allergic agents, anti-amebic agents, anti-androgen agents, anti-anemic agents, anti-anginal agents, anti-anxiety agents, anti-arthritic agents, anti-asthmatic agents, anti-atherosclerotic agents, antibacterial agents, anticholelithic agents, anticholelithogenic agents, anticholinergic agents, anticoagulants, anticoccidal agents, anticonvulsants, antidepressants, antidiabetic agents, antidiuretics, antidotes, antidyskinetics agents, anti-emetic agents, anti-epileptic agents, anti-estrogen agents, antifibrinolytic agents, antifungal agents, antiglaucoma agents, antihemophilic agents, antihemophilic Factor, antihemorrhagic agents, antihistaminic agents, antihyperlipidemic agents, antihyperlipoproteinemic agents, antihypertensives, antihypotensives, anti-infective agents, anti-inflammatory agents, antikeratinizing agents, antimicrobial agents, antimigraine agents, antimitotic agents, antimycotic agents, antineoplastic agents, anti-cancer supplementary potentiating agents, antineutropenic agents, antiobsessional agents, antiparasitic agents, antiparkinsonian drugs, antipneumocystic agents, antiproliferative agents, antiprostatic hypertrophydrugs, antiprotozoal agents, antipruritics, antpsoriatic agents, antipsychotics, antirheumatic agents, antischistosomal agents, antiseborrheic agents, antispasmodic agents, antithrombotic agents, antitussive agents, anti-ulcerative agents, anti-urolithic agents, antiviral agents, benign prostatic hyperplasia therapy agents, blood glucose regulators, bone resorption inhibitors, bronchodilators, carbonic anhydrase inhibitors, cardiac depressants, cardioprotectants, cardiotonic agents, cardiovascular agents, choleretic agents, cholinergic agents, cholinergic agonists, cholinesterase deactivators, coccidiostat agents, cognition adjuvants and cognition enhancers, depressants, diagnostic aids, diuretics, dopaminergic agents, ectoparasiticides, emetic agents, enzyme inhibitors, estrogens, fibrinolytic agents, free oxygen radical scavengers, gastrointestinal motility agents, glucocorticoids, gonad-stimulating principles, hemostatic agents, histamine H2 receptor antagonists, hormones, hypocholesterolemic agents, hypoglycemic agents, hypolipidemic agents, hypotensive agents, HMGCoA reductase inhibitors, immunizing agents, immunomodulators, immunoregulators, immunostimulants, immunosuppressants, impotence therapy adjuncts, keratolytic agents, LHRH agonists, luteolysin agents, mucolytics, mucosal protective agents, mydriatic agents, nasal decongestants, neuroleptic agents, neuromuscular blocking agents, neuroprotective agents, NMDA antagonists, non-hormonal sterol derivatives, oxytocic agents, plasminogen activators, platelet activating factor antagonists, platelet aggregation inhibitors, post-stroke and post-head trauma treatments, progestins, prostaglandins, prostate growth inhibitors, prothyrotropin agents, psychotropic agents, radioactive agents, repartitioning agents, scabicides, sclerosing agents, sedatives, sedative-hypnotic agents, selective adenosine A1 antagonists, adenosine A2 receptor antagonists (e.g., CGS 21680, regadenoson, UK 432097 or GW 328267), serotonin antagonists, serotonin inhibitors, serotonin receptor antagonists, steroids, stimulants, thyroid hormones, thyroid inhibitors, thyromimetic agents, tranquilizers, unstable angina agents, uricosuric agents, vasoconstrictors, vasodilators, vulnerary agents, wound healing agents, xanthine oxidase inhibitors, and the like, and combinations thereof.

Useful non-genetic therapeutic agents for use in connection with the present invention include, but are not limited to,
(a) anti-thrombotic agents such as heparin, heparin derivatives, urokinase, clopidogrel, and PPack (dextrophenylalanine proline arginine chloromethylketone);
(b) anti-inflammatory agents such as dexamethasone, prednisolone, corticosterone, budesonide, estrogen, sulfasalazine and mesalamine;
(c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors;
(d) anesthetic agents such as lidocaine, bupivacaine and ropivacaine;
(e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides;
(f) vascular cell growth promoters such as growth factors, transcriptional activators, and translational promotors;
(g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;
(h) protein kinase and tyrosine kinase inhibitors (e.g., tyrphostins, genistein, quinoxalines);
(i) prostacyclin analogs;
(j) cholesterol-lowering agents;
(k) angiopoietins;
(l) antimicrobial agents such as triclosan, cephalosporins, aminoglycosides and nitrofurantoin;
(m) cytotoxic agents, cytostatic agents and cell proliferation affectors;
(n) vasodilating agents;
(o) agents that interfere with endogenous vasoactive mechanisms;
(p) inhibitors of leukocyte recruitment, such as monoclonal antibodies;
(q) cytokines;
(r) hormones;
(s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin;
(t) smooth muscle relaxants such as alpha receptor antagonists (e.g., doxazosin, tamsulosin, terazosin, prazosin and alfuzosin), calcium channel blockers (e.g., verapimil, diltiazem, nifedipine, nicardipine, nimodipine and bepridil), beta receptor agonists (e.g., dobutamine and salmeterol), beta receptor antagonists (e.g., atenolol, metaprolol and butoxamine), angiotensin-II receptor antagonists (e.g., losartan, valsartan, irbesartan, candesartan, eprosartan and telmisartan), and antispasmodic/anticholinergic drugs (e.g., oxybutynin chloride, flavoxate, tolterodine, hyoscyamine sulfate, diclomine);
(u) bARKct inhibitors;
(v) phospholamban inhibitors;
(w) Serca 2 gene/protein;
(x) immune response modifiers including aminoquizolines, for instance, imidazoquinolines such as resiquimod and imiquimod;
(y) human apolioproteins (e.g., AI, AII, AIII, AIV, AV, etc.);
(z) selective estrogen receptor modulators (SERMs) such as raloxifene, lasofoxifene, arzoxifene, miproxifene, ospemifene, PKS 3741, MF 101 and SR 16234;
(aa) PPAR agonists, including PPAR-alpha, gamma and delta agonists, such as rosiglitazone, pioglitazone, netoglitazone, fenofibrate, bexaotene, metaglidasen, rivoglitazone and tesaglitazar;
(bb) prostaglandin E agonists, including PGE2 agonists, such as alprostadil or ONO 8815Ly;
(cc) thrombin receptor activating peptide (TRAP);
(dd) vasopeptidase inhibitors including benazepril, fosinopril, lisinopril, quinapril, ramipril, imidapril, delapril, moexipril and spirapril;
(ee) thymosin beta 4;
(ff) phospholipids including phosphorylcholine, phosphatidylinositol and phosphatidylcholine; and
(gg) VLA-4 antagonists and VCAM-1 antagonists.

The non-genetic therapeutic agents may be used individually or in combination, including in combination with any of the agents described herein.

Further examples of non-genetic therapeutic agents, not necessarily exclusive of those listed above, include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, alagebrium chloride (ALT-711), ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

Useful genetic therapeutic agents for use in connection with the present invention include, but are not limited to, anti-sense DNA and RNA as well as DNA coding for the various proteins (as well as the proteins themselves), such as (a) anti-sense RNA; (b) tRNA or rRNA to replace defective or deficient endogenous molecules; (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor; (d) cell cycle inhibitors including CD inhibitors, and (e) thymidine kinase ("TK") and other agents useful for interfering with cell proliferation. DNA encoding for the family of bone morphogenic proteins ("BMP's") are also useful and include, but not limited to, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently desirably BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include, but not limited to, viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers such as polyvinylpyrrolidone (PVP), SP1017 (SLPRATEK), lipids such as cationic lipids, liposomes, lipoplexes, nanoparticles, or microparticles, with and without targeting sequences such as the protein transduction domain (PTD).

Cells for use in connection with the present invention may include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis (antirestenotics). Such agents are useful for the practice of the present invention and include one or more of the following:

(a) Ca-channel blockers including benzothiazapines such as diltiazem and clentiazem, dihydropytidines such as nifedipine, amlodipine and nicardapine, and phenylalkylamines such as verapamil;
(b) serotonin pathway modulators including: 5-HT antagonists such as ketanserin and naftidrofuryl, as well as 5-HT uptake inhibitors such as fluoxetine;
(c) cyclic nucleotide pathway agents including phosphodiesterase inhibitors such as cilostazole and dipyridamole, adenylate/Guanylate cyclase stimulants such as forskolin, as well as adenosine analogs;
(d) catecholamine modulators including α-antagonists such as prazosin and bunazosine, β-antagonists such as propranolol and α/β-antagonists such as labetalol and carvedilol;
(e) endothelin receptor antagonists such as bosentan, sitaxsentan sodium, atrasentan, endonentan;
(f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine;
(g) Angiotensin Converting Enzyme (ACE) inhibitors such as cilazapril, fosinopril and enalapril;
(h) ATII-receptor antagonists such as saralasin and losartin;
(i) platelet adhesion inhibitors such as albumin and polyethylene oxide;
(j) platelet aggregation inhibitors including cilostazole, aspirin and thienopyridine (ticlopidine, clopidogrel) and GP IIb/IIIa inhibitors such as abciximab, epitifibatide and tirofiban;
(k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C;
(l) cyclooxygenase pathway inhibitors such as aspirin, ibuprofen, flurbiprofen, indomethacin and sulfinpyrazone;
(m) natural and synthetic corticosteroids such as dexamethasone, prednisolone, methprednisolone and hydrocortisone;
(n) lipoxygenase pathway inhibitors such as nordihydroguairetic acid and caffeic acid;
(o) leukotriene receptor antagonists; (p) antagonists of E- and P-selectins;
(q) inhibitors of VCAM-1 and ICAM-1 interactions;
(r) prostaglandins and analogs thereof including prostaglandins such as PGE1 and PGI2 and prostacyclin analogs such as ciprostene, epoprostenol, carbacyclin, iloprost and beraprost;
(s) macrophage activation preventers including bisphosphonates;
(t) HMG-CoA reductase inhibitors such as lovastatin, pravastatin, atorvastatin, fluvastatin, simvastatin and cerivastatin;
(u) fish oils and omega-3-fatty acids;
(v) free-radical scavengers/antioxidants such as probucol, vitamins C and E, ebselen, trans-retinoic acid, SOD (orgotein) and SOD mimics, verteporfin, rostaporfin, AGI 1067, and M 40419;
(w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives;

(x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518;

(y) cell motility inhibitors such as cytochalasin B;

(z) antiproliferative/antineoplastic agents including antimetabolites such as purine antagonists/analogs (e.g., 6-mercaptopurine and pro-drugs of 6-mercaptopurine such as azathioprine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), olimus family drugs (e.g., sirolimus, everolimus, tacrolimus, zotarolimus, etc.), cerivastatin, flavopiridol and suramin;

(aa) matrix deposition/organization pathway inhibitors such as halofuginone or other quinazolinone derivatives, pirfenidone and tranilast;

(bb) endothelialization facilitators such as VEGF and RGD peptide;

(cc) blood rheology modulators such as pentoxifylline and (dd) glucose cross-link breakers such as alagebrium chloride (ALT-711).

These therapeutic agents may be used individually or in combination, including in combination with any of the agents described herein.

Numerous additional therapeutic agents useful for the practice of the present invention are also disclosed in U.S. Pat. No. 5,733,925 to Kunz, the contents of which is incorporated herein by reference.

A wide range of therapeutic agent loadings may used in connection with the dosage forms of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

As is readily apparent, numerous modifications and changes may readily occur to those skilled in the art, and hence it is not desired to limit the invention to the a radially extendible stent for implantation in a bodily passageway, being expandable from an initial unexpanded state to an expanded state a radially expandable stent exact construction and operation as shown and described, and accordingly, all suitable modification equivalents may be resorted to falling within the scope of the invention as claimed.

What is claimed is:

1. A radially-expandable implant for implantation in a bodily passageway, said implant comprising a stent having a main body extending from an inside surface to an outside surface and from a first end to a second end thereof, said main body comprising a shape-memory polymer and being expandable from an initial unexpanded state to an expanded state, wherein said outside surface of said main body is a textured non-textile outer surface defining an outwardly extending geometric pattern, wherein said pattern comprises a diagonal cross hatch pattern, the cross hatch pattern creates valleys including raised regions, wherein the raised regions are pyramid-like regions between the valleys.

2. A radially-expandable implant as in claim 1, wherein said shape memory polymer is selected from the group consisting of polynorbonene, polycaprolactone, polyenes, nylons, polycyclooctene (PCO), blends of PCO and styrene-butadiene rubber, polyvinyl acetate/polyvinylidine fluoride (PVAc/PVDF), blends of PVAc/PVDF/polymethylmethacrylate (PMMA), polyurethanes, styrene-butadiene copolymers, polyethylene, trans-isoprene, blends of polycaprolactone and n-butylacrylate, POSS polyurethane polymers and blends thereof.

3. A radially-expandable implant as in claim 1, wherein said implant is pre-formed prior to implantation with said outwardly extending geometric pattern.

4. A radially-expandable implant as in claim 1, wherein said outwardly extending geometric pattern extends in a longitudinal direction from said first end to said second end and about the entire circumference of said implant.

5. The radially-expandable implant of claim 1, wherein the stent has a graft disposed on at least a portion of the outside surface thereof.

6. The radially-expandable implant of claim 3, wherein the stent has a graft disposed on at least a portion of the outside surface thereof.

7. An implant for implantation in a bodily passageway, the implant comprising a radially-expandable support structure, the radially-expandable support structure having a first layer extending from an interior surface to an exterior surface of said support structure, the first layer comprising a shape-memory polymer and being expandable from an initial unexpanded state to an expanded state, wherein the exterior surface of the first layer is a textured non-textile outer surface defining an outwardly extending geometric pattern, wherein said pattern comprises a diagonal the cross hatch pattern creates valleys including raised regions, wherein the raised regions are pyramid-like regions between the valleys.

8. The implant of claim 7 further comprising a graft disposed over at least a portion of the outside surface of the support structure.

* * * * *